(12) United States Patent
Brophy et al.

(10) Patent No.: US 7,405,338 B2
(45) Date of Patent: Jul. 29, 2008

(54) DEHYDROGENATION REACTIONS IN NARROW REACTION CHAMBERS AND INTEGRATED REACTORS

(75) Inventors: John H. Brophy, Bristol (GB); Anna Lee Tonkovich, Marysville, OH (US); Gary Roberts, West Richland, WA (US); Matthew B. Schmidt, Columbus, OH (US); G. Bradley Chadwell, Reynoldsburg, OH (US)

(73) Assignee: Velocys, Plain City, OH (US)

( * ) Notice: Subject to any disclaimer, the term of this patent is extended or adjusted under 35 U.S.C. 154(b) by 648 days.

(21) Appl. No.: 10/408,744

(22) Filed: Apr. 7, 2003

(65) Prior Publication Data

US 2004/0199039 A1  Oct. 7, 2004

(51) Int. Cl.
*C07C 5/333* (2006.01)
(52) U.S. Cl. .................. 585/660; 585/654; 585/920; 585/925
(58) Field of Classification Search ......... 585/660–663, 585/921, 925
See application file for complete search history.

(56) References Cited

U.S. PATENT DOCUMENTS

| | | |
|---|---|---|
| 4,739,124 A | 4/1988 | Ward |
| 4,760,210 A | 7/1988 | Sweeney |
| 4,940,826 A | 7/1990 | Font Freide et al. |
| 5,254,788 A * | 10/1993 | Gartside et al. ............. 585/659 |
| 5,811,062 A | 9/1998 | Wegeng et al. |
| 5,935,489 A | 8/1999 | Hershkowitz et al. |
| 5,997,826 A | 12/1999 | Lodeng et al. |
| 6,117,578 A | 9/2000 | Lesieur |
| 6,166,283 A | 12/2000 | Bharadwaj |
| 6,190,624 B1 | 2/2001 | Romatier |
| 6,200,536 B1 * | 3/2001 | Tonkovich et al. .......... 422/177 |
| 6,274,113 B1 | 8/2001 | Heyse et al. |
| 6,315,977 B1 | 11/2001 | Cantacuzene |
| 6,365,543 B1 | 4/2002 | Schmidt et al. |
| 6,488,838 B1 * | 12/2002 | Tonkovich et al. .......... 208/108 |
| 6,515,146 B1 | 2/2003 | Perregaard et al. |
| 6,540,975 B2 * | 4/2003 | Tonkovich et al. .......... 423/659 |
| 6,566,573 B1 | 5/2003 | Bharadwaj |
| 6,709,640 B1 | 3/2004 | Romatier et al. |
| 6,756,340 B2 | 6/2004 | Voskoboynikov et al. |

(Continued)

FOREIGN PATENT DOCUMENTS

EP  0 308 976  3/1989

(Continued)

OTHER PUBLICATIONS

PCT International Search Report, PCT/US2004/010508, mailed Sep. 28, 2004.

(Continued)

*Primary Examiner*—Glenn Caldarola
*Assistant Examiner*—In Suk Bullock
(74) *Attorney, Agent, or Firm*—Frank Rosenberg

(57) ABSTRACT

Methods of dehydrogenating hydrocarbons to yield unsaturated compounds are described. Reactor configurations useful for dehydrogenation are also described. Hydrocarbons can dehydrogenationed, for relatively long periods of time-on-stream, in a reaction chamber having a dimension of 2 mm or less to produce $H_2$ and an olefin. Techniques have been developed that reduce coke and allow stable, relatively long-term operation in small reactors.

23 Claims, 12 Drawing Sheets

U.S. PATENT DOCUMENTS

| | | | |
|---|---|---|---|
| 6,756,515 B2 | 6/2004 | Rende et al. | |
| 6,800,044 B2 * | 10/2004 | Inamura | 474/18 |
| 2003/0007904 A1 | 1/2003 | Tonkovich et al. | |
| 2004/0034266 A1 | 2/2004 | Brophy et al. | |
| 2004/0220434 A1 | 11/2004 | Brophy et al. | |

FOREIGN PATENT DOCUMENTS

| | | | |
|---|---|---|---|
| WO | WO 01/54807 | * | 8/2001 |
| WO | WO 01/54807 A1 | | 8/2001 |
| WO | WO 01/70650 A1 | | 9/2001 |
| WO | WO 02/064248 A2 | | 8/2002 |
| WO | WO 2004/016347 | | 2/2004 |
| WO | WO 2004/028685 A2 | | 4/2004 |

OTHER PUBLICATIONS

Ryu et al., "Catalytic combustion of methane over supported bimetallic Pd catalysts: Effects of Ru or Rh addition," Catalysis Today 47 pp. 141-147 (1999).

PCT International Search Report, PCT/US03/16210, mailed Jan. 3, 2004.

Bhasin et al., "Dehydrogenation and oxydehydrogenation of paraffins to olefins," Applied Catalysts A: 221 pp. 397-419 (2001).

Kursawe et al., "Comparison of Ag/Al- and Ag/Al2O3 Catalytic Surfaces for the Partial Oxidation of Ethene in Microchannel Reactors," in IMRET 5: Proceedings of the 5th Intl. Conf. On Microreaction Technology pp. 240-251 (2001).

Walter et al., "Microchannel Reaction Oxidation of Isoprene," in IMRET 5: Proceedings of the 5th Intl. Conf. On Microreaction Technology pp. 387-390 (2001).

Claus et al., "Miniaturizatoin of screening devices for the combinatorial development of heterogensous catalysts," Catalysis Today, 67, pp. 319-339 (2001).

Jones et al., "Dehydrogenation of cyclohexane to benzene in microreactors," in Microfluidic Devices and Systems II, pp. 160-168 (1999).

Beretta et al., "Production of olefins via oxidative dehydrogenation of light paraffins at short contact times," Catalysis Today, 64, pp. 103-111 (2001).

Zhou et al., "Oxidative dehydrogenation of propane over mesoporous HMS silica supported vanadia," Catalyst Letters, 75 pp. 107-112 (2001).

Steinfeldt et al., "Comparative studies of the oxidative dehydrogenation of propane in microchannels reactor module and fixed-bed reactor," Studies in Surface Science and Catalysis, pp. 185-190 (2001).

Cong et al., "Combinatorial discovery of oxidative dehydrogenation catalysts within the Mo-V-Nb-O system," Proc. Natl. Acad. Sci. USA, 96, pp. 11077-11080 (1999).

Liu et al., "Discovery from combinatorial hetergeneous catalysis A new class of catalyst for ethane oxidative dehydrogenation at low temperatures," Appl. Catal. A. 254, pp. 59-66 (2003).

Cui et al. "Fabrication of microreactors for hehydrogenation of cyclohexane to benzene," in Sensors and Actuators B—Chemical 71 pp. 228-231 (2000) abstract only.

Wolfrath et al., "Novel Membrane Reactor with Filamentous Catalytic Bed for Propane Dehydrogenation," 40, pp. 5234-5239 (2001).

Venkataraman et al., "Millisecond catalytic wall reactors: dehydrogention of ethane," Chem. Eng. Sci., 57 pp. 2335-2343 (2002).

Euzen et al., "Deactivation of palladium catalyst in catalytic combustion of methane," Catalysis Today, 47 pp. 19-27 (1999).

Kestenbaum et al., "Synthesis of ethylene oxide in a microreaction system," in IMRET 3 Proceedings of the Third international Conf. on Microreaction Technology 207-212 (1999).

* cited by examiner

DEHYDROGENATION REACTIONS IN NARROW REACTION CHAMBERS AND INTEGRATED REACTORS

FIELD OF THE INVENTION

This invention relates to dehydrogenation reactions that produce hydrogen and unsaturated compounds.

BACKGROUND

There are two leading processes developed for dehydrogenation (DH) of propane to propylene (for polypropylene) and (iso)butane to isobutene. They are both operated on a large scale. There are no commercial catalytic processes for ethane to ethylene due to the high temperatures required and coke formation.

A continuous process (UOP Oleflex) first commercialized in 1990, uses a $Pt/Sn/Al_2O_3$ catalyst in 3 adiabatic (but close to isothermal) radial flow moving bed reactors with feed pre-heat, inter-stage heating and continuous catalyst regeneration (CCR). The process gets close to thermodynamic equilibrium. Fresh feed is mixed with recycled hydrogen (to reduce coking) and unconverted feed at slightly positive pressure.

Another commercialized process (ABB Lummus Catofin), is a cyclic process that uses a $Cr_2O_3/Al_2O_3$ catalyst (activated alumina impregnated with 18-20 wt % chromium) in 3 fixed bed reactors operating under slight vacuum. While one reactor is processing feed, one has its catalyst regenerated in situ with air and the third is purged to give continuous plant throughput. Fresh and recycle feed are preheated to 550-650° C. (isobutane), or 550-750° C. for propane, and fed to the reactor at 0.35-0.7 bar pressure. During reaction, coke deposits on the catalyst and combustion of the coke during regeneration re-heats the catalyst bed.

The Steam Active Reforming process uses a $Pt/Sn/Zn/Al_2O_3$ (aluminate spinel) catalyst with steam diluent to maintain a positive pressure in the reactor and reduce partial pressure of hydrocarbons and hydrogen, favoring equilibrium. Steam also reduces coke formation and supplies heat to the reaction. Reactors are multi-tubular fixed beds in a furnace firebox to supply heat and operate isothermally to boost single pass equilibrium yields. Reactor operation is cyclic with 7 hours on line followed by 1 hour regeneration with air.

Typical parameters of these 3 processes are given in Table 1 for isobutane feeds.

TABLE 1

Characteristics of Some Prior Dehydrogenation Processes

| Process | Oleflex | STAR | Catofin |
|---|---|---|---|
| Licensor | UOP | Krupp Uhde | ABB Lummus |
| Temp (C.) | 550 | 480-630 | 540-650 |
| Pressure (bar) | >1 | 2.5-3.5 | 0.35-0.75 |
| H2/HC feed ratio | 3 | 0-2 | 0 |
| Steam/HC ratio | 0 | 4(2-10) | 0 |
| LHSV (h-1) | 4 | 4 | 0.4-2 |
| Conversion (%) | ~35 | 40-55 | 65 |
| Selectivity (%) | 91-93 | 88-92 | 90 |
| Heat input | Inter-stage heating | Furnace | Catalyst regeration |
| Regeneration | Moving bed | Cyclic | Cyclic |
| Cycle time | 2-7 days | 7-8 hours | 5-15 minutes |
| Catalyst | $Pt/Sn/Al_2O_3$ | $Pt/Sn/Zn/Al_2O_3$ | $Cr2O3/Al_2O_3$ |
| Catalyst life | 1-2 years | 1-2 years | 1.5-3 years |

Venkataraman et al., in "Millisecond catalytic wall reactor: dehydrogenation of ethane," *Chem. Eng. Sci.*, 57, 2335-2343 (2002), studied the dehydrogenation of ethane in a stream of steam and ethane run in a 4 mm inner diameter tube without a catalyst. Heat was added from combustion in a 1 mm gap between the outside of the inner tube and the inner surface of an outer tube. The authors concluded that this reactor, as compared with a conventional steam cracker, gave superior performance in terms of residence time and ethylene yield.

Ethane cracks cleanly at high temperatures; however, for propane and higher hydrocarbons, cracking is known to be less selective and prone to coking.

Wolfrath et al., in "Novel Membrane Reactor with Filamentous Catalytic Bed for Propane Dehydrogenation," *Ind. Eng. Chem. Res.*, 40, 5234-5239 (2001), studied propane dehydrogenation through a reactor filled with catalytic filaments. Flow through the reactor is illustrated as flowing between the catalyst filaments. In this study, a $H_2$-permeable membrane separates 2 adjacent, filament-filled catalytic beds. During operation, propane was dehydrogenated in one bed while catalyst is regenerated in the adjacent bed. Coking caused significant loss of catalytic activity. Without the membrane, an initial conversion of $X_{eq}=0.24$ decreased to 0.14 during the first 100 min on stream and 0.12 after 250 minutes. In the membrane reactor, "propane conversion decreased from 0.34 initially to about 0.2" within the first 50 minutes. The faster rate of deterioration in the membrane reactor was due to faster coke formation as a result of the lower $H_2$ concentration.

Besser et al., in "Hydrocarbon Hydrogenation and Dehydrogenation Reactions in Microfabricated Catalytic Reactors," which appeared on the internet at attila.stevens-tech.edu/~xouyang/research.htm, reported on hydrogenation and dehydrogenation of cyclohexane through 0.1 mm×0.1 mm microchannels containing a 20 nm thick Pt layer. The authors observed that the dehydrogenation would not proceed unless some $H_2$ was present initially. The authors also reported that higher temperatures favored dehydrogenation and that above 120° C., a transformation in catalyst conditions occurs which leads to a decline in activity. The authors observed a strong effect of residence time on benzene yield, with increased production at higher residence times. Other than the above-mentioned decrease in catalytic activity above 120° C., this paper does not provide data on coking or the stability of the catalytic system; however, since the experiments were conducted with fresh reactors and data was acquired "as rapidly as possible" to minimize time dependent effects, it appears that the reactors degraded quickly.

Jones et al., briefly reported on the dehydrogenation of pure cyclohexane in a microreactor in which the feed pressure was 150 kPa while the exit pressure was 1 Pa, with a residence time of 1.125 seconds. Conversions were either 7-9% or 2-3%.

SUMMARY OF THE INVENTION

Dehydrogenation produces olefins that are more reactive and susceptible to forming coke than the alkane feedstock, especially at the relatively high temperatures used in dehydrogenation. Coke formation on the catalyst causes catalyst deactivation and reduces product yields. Coke formation in the reactor or in downstream equipment can cause blockages and pressure build up in the reactor that favours reactions such as formation of methane and further coke formation again reducing the yield of useful products and causing premature shutdown of the equipment to remove the coke. We have discovered several means of reducing coking in both the catalyst bed and in downstream equipment.

DH is very endothermic and requires the transfer of large amounts of heat into the catalyst bed. It is also equilibrium limited and requires a high temperature to be maintained in the bed to achieve economic levels of conversion. Conventional fixed bed reactors are limited by heat transfer from external furnaces and operate with interstage heat exchangers, feed pre-heating, or by burning off coke on the catalyst to generate heat in the catalyst bed. All commercial systems are limited to relatively short catalyst life typically 5-15 minutes to 7-8 hours in reaction regeneration systems and up to a few days in continuous catalyst regeneration (recirculating catalysts bed) systems. In all cases catalyst activity falls off appreciably within this period.

Shorter residence times (higher LHSV) would be desirable to prevent the olefinic products reacting further to form coke but are not practical in conventional systems since increasing the rate at olefins are formed simply increases the endothermic load on the reactor and lowers the temperature even faster, thereby reducing product yields and requiring shorter cycle times or additional inter-stage charge heating. Both of which increase process costs.

We have found that dehydrogenation reactions in a microchannel reactor, surprisingly, produced higher conversions than the fixed bed at the same space velocities and higher conversions and yields even when operating at space velocities higher (at least 5 times higher LHSV) than a conventional fixed bed reactor. We have found that in a microchannel reactor, the high heat transfer into the catalyst bed allows use of very short residence times (high LHSV) without any sacrifice of conversion and with no loss of catalyst activity. Data presented below shows that the microchannel reactor can be operated at an LHSV of 157 and still achieve substantially higher conversion and yield of olefins than a conventional fixed bed reactor operating at much lower LHSV.

Conventional dehydrogenation reactions are typically diluted with hydrogen to both improve the local heat transfer and reduce the thermodynamic driving potential to solid carbon formation. Conventional wisdom would suggest that dehydrogenation in microchannel reactors would result in coking and clogging of the michrochannels. Surprisingly, it has been discovered that dehydrogenation reactions can be conducted in microchannels with stable production rates over time. Further, microchannel reactors may allow for the operation with reduced, minimal, or no hydrogen co-fed with the hydrocarbon without the unwanted co-production of coke.

In a first aspect, the invention provides a method of dehydrogenating a hydrocarbon, comprising: passing a reactant stream comprising a gaseous hydrocarbon through a reaction chamber comprising a dehydrogenation catalyst and wherein the reaction chamber has an internal dimension of 2 mm or less; and dehydrogenating the hydrocarbon within the reaction chamber to form a product stream comprising an olefin. This method includes at least one coke-reducing step selected from: quenching the product stream as it exits the reaction chamber, passing the reactant stream and/or product stream over a passivated surface in the flow path, and/or when the hydrocarbon comprises a C3 hydrocarbon or higher, passing the reactant stream into the reaction chamber at a liquid hourly space velocity (LHSV) of at least 4.

In another aspect, the invention provides a method of dehydrogenating a hydrocarbon, including: passing a reactant stream comprising a gaseous hydrocarbon into a reaction chamber containing a dehydrogenation catalyst and dehydrogenating the hydrocarbon within the reaction chamber to form a product stream comprising an olefin; wherein after at least 10 hours of continuous operation, at least 75% of the equilibrium conversion of the hydrocarbon to an olefin is achieved. In this method, the reaction chamber has an internal dimension of 2 mm or less, and the reactant stream is passed into the reaction chamber at a LHSV of at least 4. "Equilibrium conversion" is the conversion at equilibrium expected under the conditions at which the process is conducted.

In a further aspect, the invention provides a method of dehydrogenating a hydrocarbon, in which a reactant stream including a gaseous hydrocarbon flows into a reaction chamber comprising a dehydrogenation catalyst and the hydrocarbon is dehydrogenated the within the reaction chamber to form a product stream comprising an olefin. This method is further characterized in that the yield of olefin decreases by less than 50% at from 0.2 and 20 hours of continuous operation without regeneration. In this method, the reaction chamber has an internal dimension of 2 mm or less.

In a further inventive aspect, a method of conducting a reaction within an integrated reactor is disclosed, comprising: flowing a first process stream into a first reaction channel in an integrated reactor; wherein the first reaction channel comprises a first preheat zone, a first reaction chamber, and a first exhaust zone; wherein the first reaction chamber comprises a first catalyst; wherein the integrated reactor comprises a stack comprising a first reaction channel, a heat exchange channel, and a second reaction channel; conducting a reaction within the first reaction chamber to form a first stream comprising a first product; flowing a second process stream into a second reaction channel in an integrated reactor; wherein the second reaction channel comprises a second preheat zone, a second reaction chamber, and a second exhaust zone; wherein the second reaction chamber comprises a second catalyst; conducting a reaction within the second reaction chamber to form a second stream comprising a second product; wherein the first process stream flows in a first direction and the second process stream flows in a second direction, wherein the first direction is opposite the second direction; flowing a heat transfer fluid in a heat exchange channel; wherein the heat exchange channel is disposed between the first channel and the second channel, and wherein flow of the heat transfer fluid in the heat exchange channel is perpendicular to the first and second directions; wherein the heat exchange channel is adjacent to the first reaction chamber and is adjacent to the second reaction chamber, but is not adjacent to: the first preheat zone, the second preheat zone, the first exhaust zone, and the second exhaust zone; wherein heat in the heat transfer fluid is transferred to the first and second reaction chambers; wherein the temperature of the first process stream in the first preheat zone is less than the temperature in the second exhaust zone; and wherein the temperature of the second process stream in the second preheat zone is less than the temperature in the first exhaust zone. For inventions directed to dehydrogenations, the first process stream comprises a hydrocarbon, the second process stream comprises a hydrocarbon, the catalyst is a dehydrogenation catalyst, and the heat transfer fluid is a heating stream (in some preferred embodiments a combustion stream), and hydrocarbon in each process stream is converted to an unsaturated hydrocarbon. For methods of the invention in which an exothermic reaction occurs in the first and second process streams, the relative temperatures in the preheat and exhaust zones may (or may not) be reversed.

In another aspect, the invention provides a method of dehydrogenating a hydrocarbon, comprising: flowing a process stream comprising a first gas comprising a hydrocarbon into a reaction chamber; wherein the reaction chamber comprises a dehydrogenation catalyst and reaction chamber walls; wherein there is at least one aperture along the length of the reaction chamber in at least one of the reaction chamber walls; flowing a second gas through the aperture into the reaction chamber; and dehydrogenating the hydrocarbon to form an unsaturated compound and hydrogen.

In yet another aspect, the invention provides a method of conducting a reaction in an integrated reactor. In this method, a process stream flows in a first direction in a first channel in an integrated reactor. This process stream contains a reactant. The integrated reactor includes a process channel that includes a forward process channel adjacent to, and connected to a return process channel. The process channel contains at least one reaction chamber that contains a catalyst. The integrated reactor also contains at least one heating channel that is adjacent to the forward process channel or the return process channel. A heat transfer fluid flows through the heat transfer fluid flow channel. Reactant converts to a product in the reaction chamber. In this method, the process stream flows in a second direction in the return process channel. The second direction is opposite the first direction. Heat transfers between the stream in the forward process channel and the return process channel. In some preferred embodiments, the heat transfer channel comprises a forward heat transfer fluid flow channel connected to a return heat transfer fluid flow channel. For inventions directed to dehydrogenations, the process stream comprises a hydrocarbon, the catalyst is a dehydrogenation catalyst, the heat transfer fluid is a heating stream (in some preferred embodiments a combustion stream), hydrocarbon in the process stream is converted in the reaction chamber to an unsaturated hydrocarbon, and there is net heat flow from the heat transfer fluid flow channel into the process channel.

Various embodiments of the present invention may provide advantages, such as one or more of the following: lower cost, less complex processes and/or apparatuses, fewer moving parts, reducing or eliminating the need for interstage heating, capability of long time on stream (TOS) without regeneration, durability, stability, low coking, achievement of desired performance such as conversion, selectivity, etc., high liquid and gas hourly space velocities, ability to operate under a variety of conditions including temperature, pressure and reactant composition, and compactness.

Performance advantages in the use of microreactors in the present invention include their relatively large heat and mass transfer rates. Unlike conventional reaction vessels, microchannel reactors can achieve better temperature control, and maintain a relatively more isothermal profile. This, in turn, advantageously leads to lessened peak temperatures and lessened coking of the hydrocarbon starting material and/or desired product. Better temperature control also reduces unselective homogeneous gas phase reations.

Glossary

The "average heat exchanger residence time" is defined as the internal volume of a heat exchanger or portion of a heat exchanger divided by the average of the actual volumetric flowrate of gaseous product at the heat exchanger inlet temperature and pressure and the heat exchanger outlet temperature and pressure. The "internal volume of a heat exchanger or portion of a heat exchanger" that is used for calculating volumetric flowrate is the volume of a heat exchanger that is adjacent to a product stream as described below. One dimension of the heat exchanger begins on one edge defined by the line where a heat exchanger is adjacent to a reaction chamber (near this line, the heat exchange fluid is colder than the process stream) and ends at an edge of the heat exchanger channel that is adjacent to the product outlet. Over this dimension of the heat exchanger (for a 90° cross-flow arrangement, this dimension is the width of a heat exchanger channel), the product mixture is cooled from the reaction (i.e., the process stream) temperature at the beginning of the heat exchanger volume to the product outlet temperature. The heat exchanger inlet is defined as beginning at an area through the heat exchanger where a fluid flowing through the heat exchanger first "contacts" (i.e., becomes adjacent to) the product stream (for a cross-flow heat exchanger, this area is perpendicular to flow). The heat exchanger outlet is defined as ending at an area through the heat exchanger where a fluid flowing through the heat exchanger last "contacts" (i.e., is adjacent to) the product stream. The "product outlet" is either the device outlet, or, in an integrated device, the point at which the product stream is subjected to another unit operation (other than cooling and/or change in pressure); whichever comes first. The "internal volume of a heat exchanger" is also the volume over which flowrate, temperatures, and pressures are measured or calculated. "Adjacent" means directly adjacent such that a wall separates two channels or chambers; this wall may vary in thickness; however, "adjacent" chambers are not separated by an intervening chamber that would interfere with heat transfer between the chambers.

By "including" is meant "comprising", however, it will be understood that the terms "consists of" or "consists essentially of", may alternatively be used in place of "comprising" or "including" to describe more limited aspects of the invention. "Integrated" means all the components are within the same structure wherein the exhaust zones are directly connected to the reaction chambers.

Liquid hourly space velocity (LHSV) is defined based on the liquid volumetric flow and the reaction chamber volume. Reaction chamber volume is defined as the volume of a process channel where catalyst is present and the temperature is sufficiently high for dehydrogenation to occur. Reaction chamber volume is the wall-to-wall volume and includes catalyst volume (including pore volume, and, if present, interstitial volume), and, if present, the volume of a bulk flow path or paths adjacent to the catalyst. For dehydrogenation of isobutene, a "sufficiently high" temperature will typically be at least about 400° C., for dehydrogenation of propane, typically at least about 450° C. To calculate LHSV, GHSV (h−1), defined as flow rate of gas of hydrocarbon (ml/h) per volume catalyst (ml), is calculated and then it is divided by a factor of 230. This factor takes into account the difference in the density of the hydrocarbon in liquid and gas phase. The contact time is calculated as 3600/GHSV(hydrocarbon) and has dimensions of the seconds. "A reactant stream containing a hydrocarbon" can also be termed "a hydrocarbon stream," and, in the context of the present invention, these terms mean the entire gas stream (not merely a selected portion thereof) entering a reaction chamber(s).

Definitions of the performance parameters used herein, are as follows. "Percent conversion" refers to the moles of organic compound to be dehydrogenated (e.g., moles of alkane) that is consumed, based on the moles of the said organic compound fed to the reactor. "Percent selectivity" refers to the moles of carbon in the products (e.g., alkene) formed based on the moles of the said organic compound consumed. "Percent yield" refers to the moles of desired product (e.g., alkene) formed based on the moles of the said organic compound fed. For reaction mixtures of ethane, propane or butane, desired products are ethene, propene, and butenes, respectively. Percent selectivity and percent yield are based on carbon. To give a hypothetical example, for a reaction mixture containing 2 moles of hexane and 1 mole ethane that results in a product mixture containing 1 mole hexane, 1 mole ethene, 0.5 mole hexene, 2 mole $CO_2$ and 0.33 mole propene would have a 57% conversion with a (6 mol C)/(8 mol C)=75% selectivity and 50% yield.

DESCRIPTION OF PREFERRED EMBODIMENTS

Figure 1:
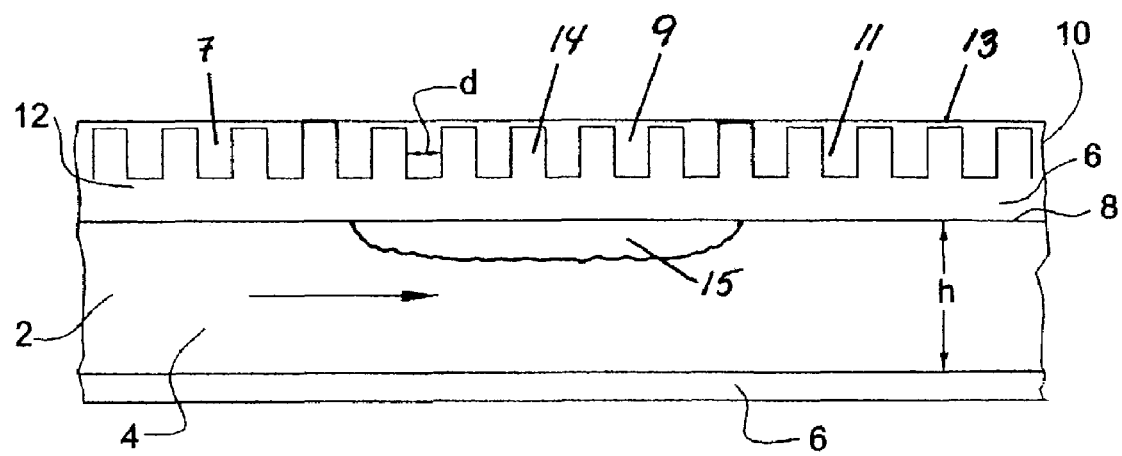
FIG. 1 is a representational, cross-sectional view of apparatus that can be utilized in the present invention.

The reactant stream containing a hydrocarbon contains at least one hydrocarbon that is capable of being dehydrogenated to yield $H_2$ and a carbon-carbon multiple bond as its principal products. Preferred examples of hydrocarbons are $C_2$-$C_{18}$ alkanes, preferably $C_2$-$C_{10}$ alkanes, isobutene, propane, ethane, or $C_{10}$-$C_{15}$ alkanes such as could be used for making detergent alcohols. The alkanes can be linear, branched and cyclic. Hydrocarbons can be obtained commercially either in pure form or in mixtures. Hydrocarbons can also be derived from other reactions, and the output of these reactions used with or without an intervening purification step.

The reactant stream may contain nonreactive diluents such as nitrogen or other inert gases. The reactant stream may contain chemically reactive diluents such as hydrogen and carbon dioxide. Steam is not needed (i.e., there can be no steam, or essentially no steam). Steam, if present, is preferably present in a steam:C ratio of 10 or less, more preferably 5 or less, and in some embodiments 2-10. The reactant stream does not contain significant amounts of oxidants such as would alter the product distribution or catalyst life by more than 10%. The total diluents to dehydrogenatable hydrocarbons molar ratio is preferably 10:1 or less, more preferably 2:1 or less, in some embodiments, essentially no diluents. In some preferred embodiments, the hydrocarbons in the reactant stream are at least 75 mol %, more preferably at least 90 mol % of a single type of hydrocarbon (propane, for example). In some preferred embodiments, the reaction contains no diluent except $H_2$. In some embodiments, there is no $H_2$ in the reactant stream, in some embodiments there is a 0 to 5 $H_2$:hydrocarbon ratio on a molar basis. It is believed that $H_2$ need not be initially present for the system to operate. Hydrogen may be fed from a separate source or produced in the reaction and recycled.

The reaction temperature will depend on the composition of the reactant stream. Use of microchannel apparatus enables fast and uniform heat transfer; conducting the dehydrogenation at high temperature and high velocity enables higher single pass conversion without coking. For dehydrogenation of iso-butane, temperature in the reaction chamber is preferably in the range of 400 to 650° C., more preferably 450 to 550° C. For propane DH, temperature in the reaction chamber is preferably in the range of 450 to 700° C., more preferably 500 to 700° C.

Liquid hourly space velocity (LHSV) preferably is at least 4 $h^{-1}$; more preferably at least 16 $h^{-1}$; more preferably at least 64 $h^{-1}$; more preferably at least 132 $h^{-1}$. In other preferred embodiments, LHSV ranges from 16 $h^{-1}$ to 200 $h^{-1}$ based on the reaction chamber volume (this is where catalyst is present and could be the volume of a packed catalyst or a catalyst wall coating or catalyst insert and the bulk flow path past the coating or insert). Contact times preferably are in the range of 0.001 to 5 s, more preferably 0.001 to 1 sec.

Short residence time in the reaction chamber and/or downstream pipework is desirable to minimize coke formation. Thus, in preferred embodiments, the fluid flow rate in the downstream pipework is the same or higher than in the reaction chamber. In some preferred embodiments, residence time in the downstream piping is 50 ms or less.

Pressure inside the reactor should be low to obtain higher yields; alternatively, the partial pressure of $H_2$ can be kept low by selective removal during reaction such as by use of a $H_2$-permeable membrane. In some embodiments, pressure in the reactor is 10 bar or less; more preferably 2 bar or less.

In some preferred embodiments, pressure drop through the reactor, or through a reaction channel, is 2 bar or less, more preferably 0.5 bar or less.

In this invention, "microchannel reactors" are characterized by the presence of at least one reaction channel having a dimension (wall-to-wall, not counting catalyst) of 2.0 mm (preferably 1.0 mm) or less, and in some embodiments 50 to 500 μm. Both height and width are perpendicular to the direction of flow. The height and/or width of a reaction microchannel is preferably 2 mm or less, and more preferably 1 mm or less. The length of a reaction channel is parallel to flow through the channel and is typically longer than height and width. Preferably, the length of a reaction chamber is greater than 1 cm, more preferably in the range of 1 to 100 cm. Typically, the sides of the reaction channel are defined by reaction channel walls. These walls are preferably made of a hard material such as a ceramic, an iron based alloy such as steel, or a nickel-based alloy. In some preferred embodiments, the reaction chamber walls are comprised of stainless steel or inconel which is durable and has good thermal conductivity.

In addition to the reaction channel(s), additional features such as microchannel or non-microchannel heat exchangers may be present. Microchannel heat exchangers are preferred. Adjacent heat transfer microchannels enable temperature in the reaction channel to be controlled precisely to promote selective dehydrogenation and minimize unselective reactions in the gas phase. The thickness of a wall between adjacent process channels and heat exchange channels is preferably 2 mm or less. Each of the process or heat exchange channels may be further subdivided with parallel subchannels.

The heat exchange fluids can be gases or liquids and may include steam, liquid metals, or any other known heat exchange fluids—including fluids that undergo a phase change in the heat exchanger. An improvement to heat transfer would be the use of a higher heat capacity fluid, such as a molten salt or hot oil. A hot oil is typically limited to systems with reaction temperatures no greater than 400° C. and the molten salts would be used for much higher temperatures. Especially preferred heat exchangers include combustors in which a fuel is oxidized to produce heat for the dehydrogenation reaction. The incorporation of a simultaneous exothermic reaction to provide an improved heat source can provide a typical heat flux of roughly an order of magnitude above the convective cooling heat flux.

The amount of heat that can be transferred through a plane separating the process reaction chamber from a heat exchanger is a function of the method of heat transfer. For convective heat transfer from a hot fluid in a heat exchange channel to a dehydrogenation reaction chamber, the amount of heat (as defined as Watts per square cm of reaction chamber wall area that is adjacent to the heat exchanger) transferred for a gaseous heat transfer fluid is preferably at least 1 $W/cm^2$ and may be up to about 15 $W/cm^2$. For a liquid heat transfer fluid used in convective heat transfer, higher heat transfer fluxes are achievable and may range from at least 1 $W/cm^2$ to about 30 $W/cm^2$. For conductive heat transfer from an exothermic reaction, much higher rates of heat transfer are attainable and heat flux may range from about 10 $W/cm^2$ to about 100 $W/cm^2$. These defined ranges of heat fluxes are for steady-state operation and average over the area of a process reaction chamber wall that is adjacent to a heat exchanger; or, in a reactor with multiple channels (more than two channels), an average over the areas of all dehydrogenation reaction chambers adjacent to heat exchanger(s) in all the channels in operation.

The flow of a fluid through a heat exchanger may be cross flow, counter-flow or co-flow with flow through a reaction chamber. Coflow may be preferred to obtain the greatest heat flux in the beginning of a reaction chamber if the process reaction will be greatest at the front of the reaction chamber where reactants are most concentrated.

The reactors preferably include a plurality of microchannel reaction channels and/or a plurality of adjacent heat exchange microchannels. A plurality of microchannel reaction channels may contain, for example, 2, 10, 100, 1000 or more channels. In some preferred embodiments, multiple heat exchange layers are interleaved with multiple reaction microchannels (for example, at least 10 heat exchanger layers interleaved with at least 10 layers of reaction microchannels. Typically, flow into and/or out of some or all of a plurality of reaction channels passes through a manifold or manifolds that combines the fluid flow. In preferred embodiments, microchannels are arranged in parallel arrays of planar microchannels.

Preferred reactors usable in the present invention include those of the microcomponent sheet architecture variety (for example, a laminate with microchannels). Examples of integrated combustion reactors that could be used in the present invention are described in U.S. patent application Ser. No. 10/222,196, filed Aug. 15, 2002, which is incorporated herein by reference. Some other suitable reactor designs and methods of making reactors are disclosed in U.S. patent application Ser. No. 10/306,722, filed Nov. 27, 2002, which is also incorporated herein by reference.

A simplified representational view of an apparatus of some embodiments of the present invention is illustrated in FIG. 1. The views shown in the figures are representative examples and should not be understood to limit the invention. A process channel 2 contains a bulk flow path 4. The reaction chamber is defined on two sides by reaction chamber walls 6 and 6'. The internal dimension h (height) is the distance from the surface of the metal wall 8 to the surface of the metal in the opposing wall and does not include the thickness of any oxide layer (not shown). A heating chamber 10 is adjacent to process channel 2. The illustrated heating chamber has fins 11 having a thickness d interleaved with heating channels 14 and a gap 12 between the fins and the channel wall 6. In preferred embodiments, the distance between fins and/or the thickness of the heating chamber is 2 mm, more preferably 1 mm or less. The illustrated embodiment is cross-flow; however, co-flow and counter-flow may also be employed. In some preferred embodiments, an exothermic reaction is occurring in the heating channel; however, a hot, non-reacting stream could alternatively be used. In some embodiments, the heating chamber 10 is divided into several parts, for example regions 7, 9, 13 into which various fluids could flow to tailor the temperature profile in a process channel. For example, steam or the return portion of a combustion stream could flow through region 7 to provide a preheat zone; a combustion stream can flow through region 9 to provide heat to drive the dehydrogenation reaction in a reaction chamber (a portion of the process channel in which catalyst 15 is present), and a cold fluid flows through region 13 to quench the reaction.

Figure 2B:
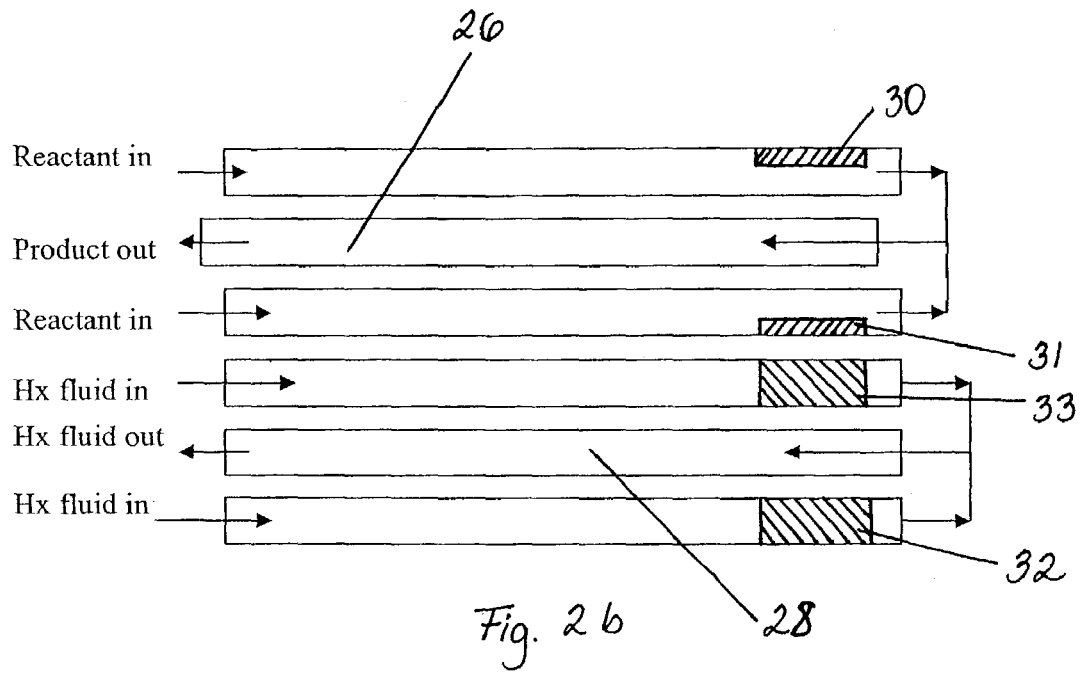
FIGS. 2A and 2B are schematic illustrations of integrated reactor designs showing the process and heat exchange channels and flows.
Figure 2A:
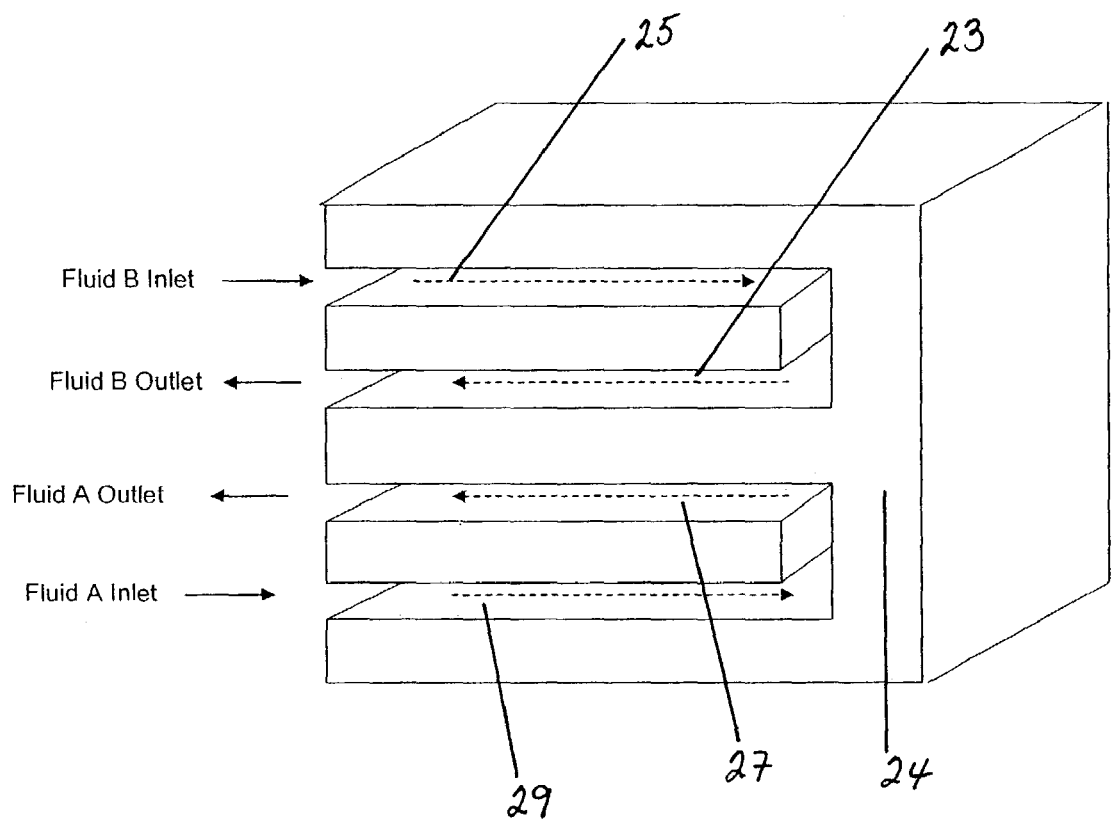

Another schematic illustration of a cross-section of an integrated reactor design is illustrated in FIG. 2A. A reactant (hydrocarbon) flows into the inlet (Fluid B inlet) of a forward process channel, passes through a u-turn, and then flows in the reverse direction in the return process channel. At the same time, a heat transfer fluid flows into the inlet (Fluid A inlet) of a heat transfer channel, passes through a u-turn, and then flows in the reverse direction in the return heat transfer channel. It is desirable to match the hottest portion of the heat transfer channel with the reaction chamber portion of the process channel. In a preferred embodiment, the reaction chamber is located in the return process channel in an area 23 located near the u-turn (closer to the u-turn than the outlet) so that the reactant stream flowing through the forward process channel 25 is warmed by the return process stream (which could be termed the "exhaust" (i.e., the product stream) and the reaction chamber). More preferably, the heat transfer fluid is a combustion stream containing a fuel and an oxidant that is combusted in a catalyst-containing portion located in the return heat transfer channel in an area 27 located near the u-turn opposite the endothermic reaction chamber; in which case the combustion stream in the forward heat transfer channel 29 is preheated by the combustion chamber (the area where there is combustion catalyst and combustion occurs) and exhaust stream. This type of reactor design is especially desirable where the u-turn end 24 (i.e., the hot end) is relatively unconstricted so that it can expand when the device is in operation, manifolds can be connected at the inlet end (i.e., the cold end). As is true of all the reactor designs described herein, the illustrated reactor can be stacked to increase reactor capacity; for example three of the illustrated reactors can be stacked in a single integrated device to have six layers: heat exchange: process: heat exchange: process: heat exchange: process; preferably with all the inlets and outlets located on one side of the device. In some preferred embodiments, the u-turns connect to a single return channel and are not manifolded.

An alternative design is illustrated in FIG. 2B in which return channels 26, 28 are disposed between forward channels. The operation of this device is analogous with the reactor of FIG. 2A, except in preferred embodiments the respective catalysts are located in the forward process 30, 31 and heat exchange channels 32, 33 near the u-turns. Although the catalysts are depicted as partially filling a cross-section of a process channel (such catalysts could be, for example, catalytic inserts or wall coatings), catalysts may also fill a cross-section of a process channel (such as, for example, a packed bed).

Figure 3A:
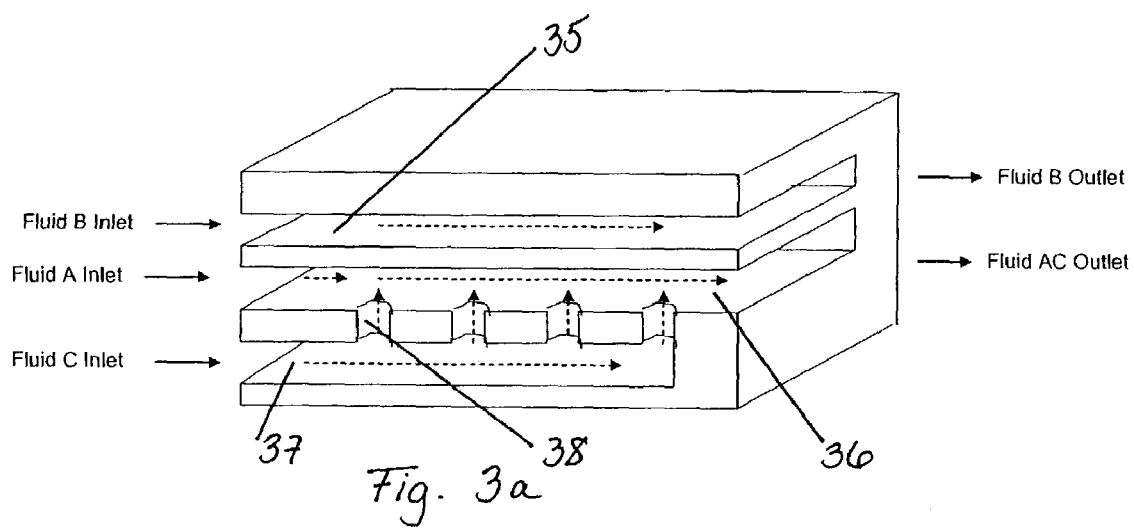
FIGS. 3A-3C are schematic illustrations of integrated reactor designs showing the process and heat exchange channels with distributed flow.
Figure 3B:
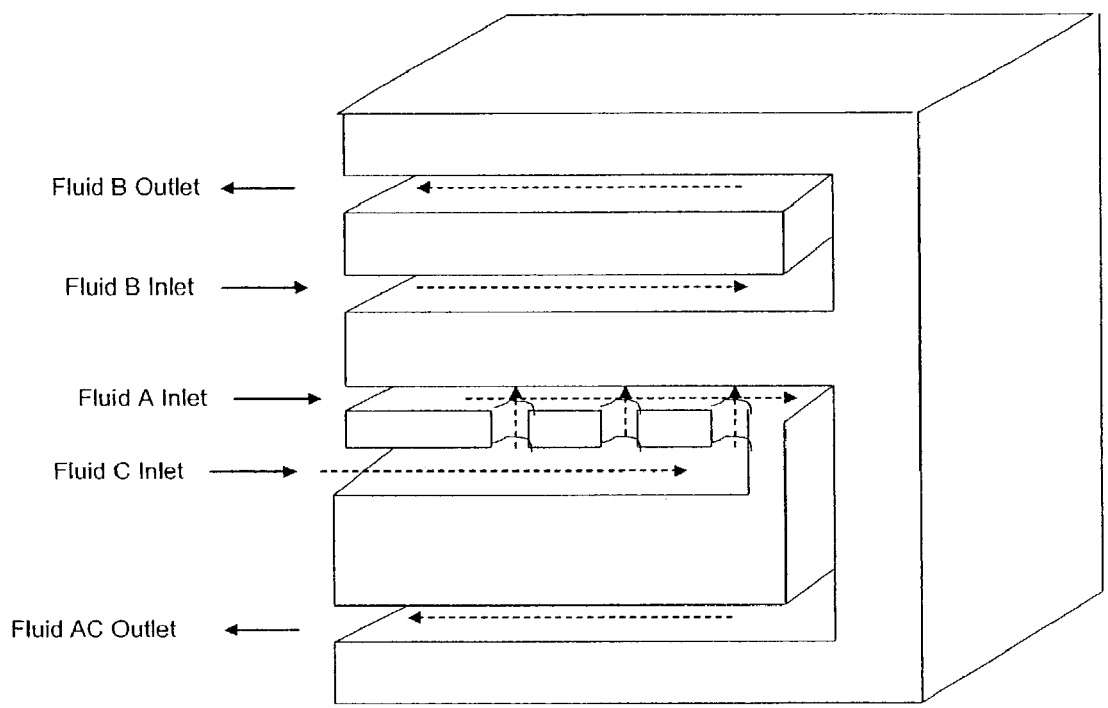
Figure 3C:
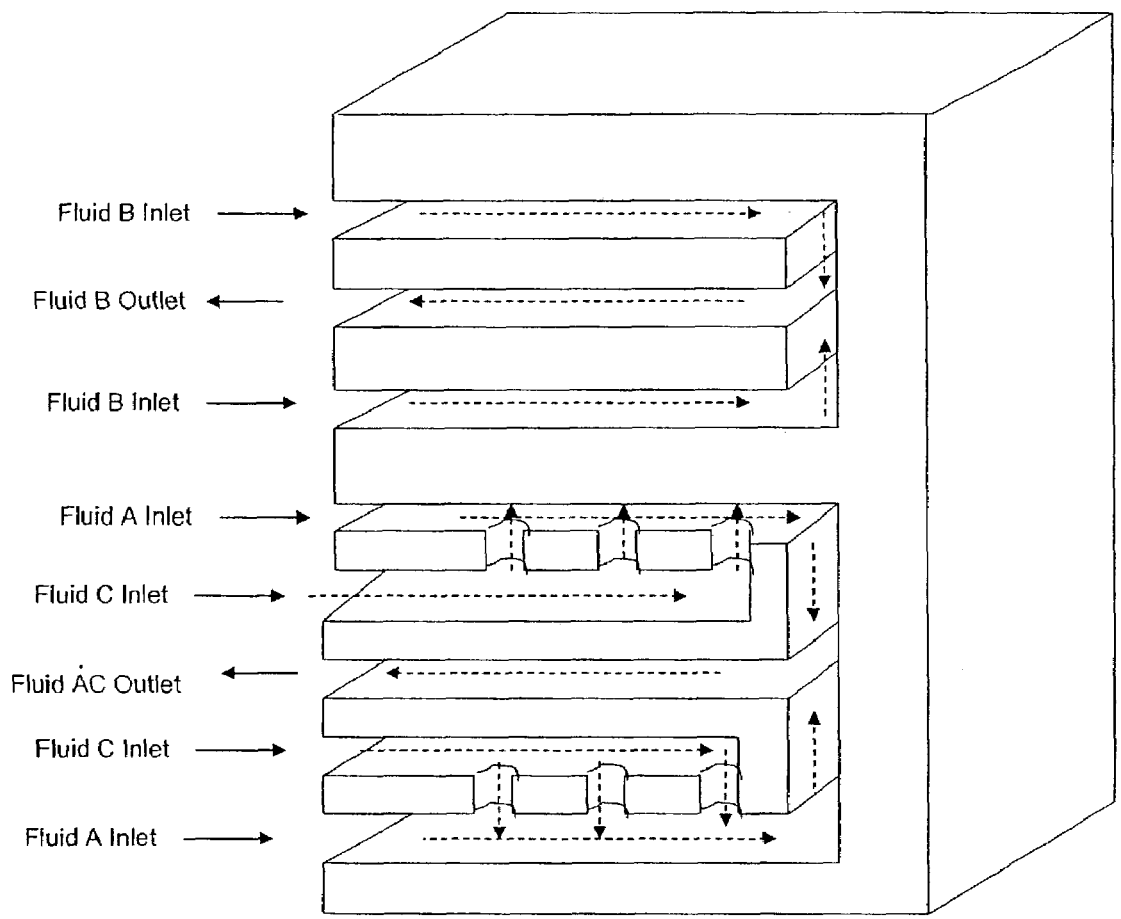

Reactor designs illustrating the distributed flow concept are illustrated in FIGS. 3A-3C. In distributed flow, a secondary fluid enters into a reaction chamber (which may also be a combustion chamber). FIG. 3A illustrates a device in which a first fluid (Fluid B) flows through a first channel 35. Adjacent to this channel is a second channel 36 into which feeds Fluid A. Fluid C enters the reactor in a separate channel 37 and then flows in a distributed fashion through apertures 38 along the length of the second channel. In some embodiments, the first channel contains a dehydrogenation catalyst (not shown) and a hydrocarbon flows into the channel. In some embodiments, the second channel contains a combustion catalyst (not shown) and either a fuel or an oxidant flows into the inlet of the second channel (Fluid A Inlet) while, at the same time, an oxidant or fuel flows into a third channel (Fluid C Inlet) and flows through apertures 38 into the combustion chamber where there is a combustion reaction at or near the wall separating the first and second channels. This controls the rate of combustion and matches the heat generation rate with the heat required to drive the endothermic reaction. Any thermal profile can be tailored. Additional details of this type of integrated combustion are discussed in incorporated U.S. patent application Ser. No. 10/222,196.

Alternatively, a heat transfer fluid (Fluid B) can pass through the first channel. In some preferred embodiments, the first channel 35 contains a combustion catalyst (not shown) and Fluid B contains a mixture of fuel and oxidant. A reactant (hydrocarbon) can flow in through either inlet (Fluid A Inlet or Fluid C Inlet) and react over a (dehydrogenation) catalyst in the second channel 36. When hydrocarbon enters into the third channel 37 (through Fluid C Inlet) it flows in a distributed fashion into the second channel for a controlled reaction over the length of the reaction chamber; in this case, a secondary fluid flows through the second channel. Alternatively, a (hydrocarbon) reactant stream enters through Fluid A Inlet while a secondary fluid enters Fluid C Inlet and flows into the reaction chamber in a distributed fashion through the apertures. The secondary fluid can be reactive (a hydrocarbon, or, in the case of oxidative dehydrogenation, an oxidant) or a nonreactive diluent. A nonreactive diluent can quench the reaction. Diluents such as steam or hydrogen reduce the tendency of coke to form, and adding in a distributed fashion reduces coke in the area where coke poses the biggest problem—in the later part of the reaction chamber and the downstream piping. The secondary fluid can also have an important role for controlling temperature in the reaction chamber. A hot secondary fluid (preferably a diluent) can be added to boost conversion of the hydrocarbon. A cold secondary fluid can be effective in rapidly quenching a reaction.

Alternative designs are illustrated in FIGS. 3B and 3C in which flows can be controlled as have been described in FIG. 2 and FIG. 3A. Channels have been illustrated as open channels but it should be recognized that the channels may contain features such as catalysts, microchannel grooves, and/or support ribs.

Figure 4A:
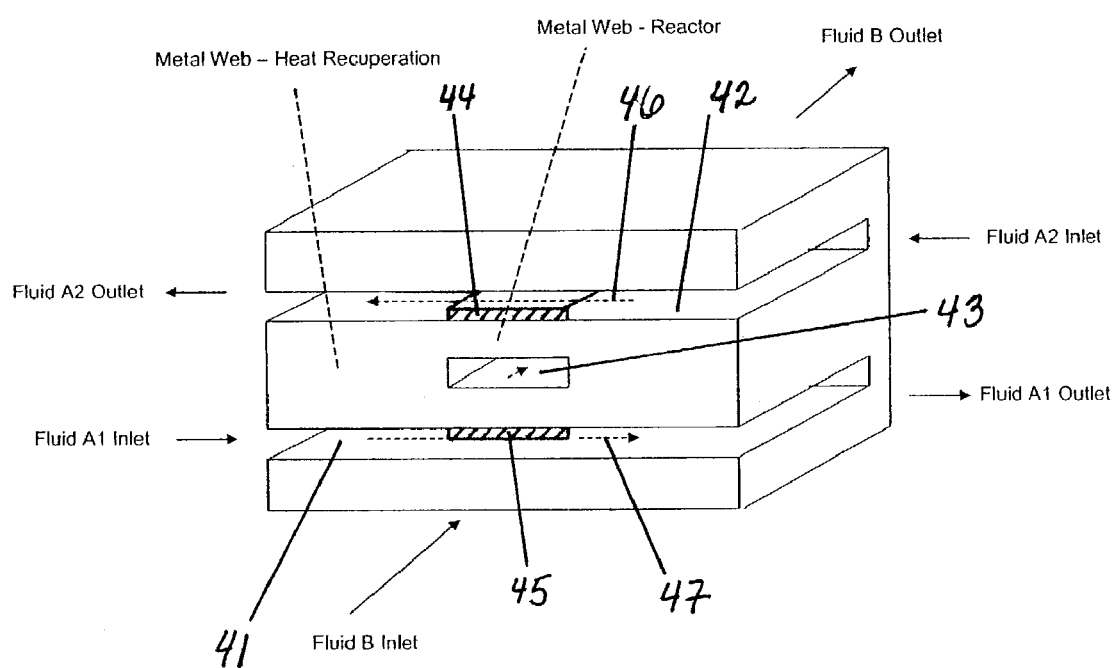
FIGS. 4A and 4B are schematic illustrations of integrated reactor designs with recuperative heat exchange between process streams.
Figure 4B:
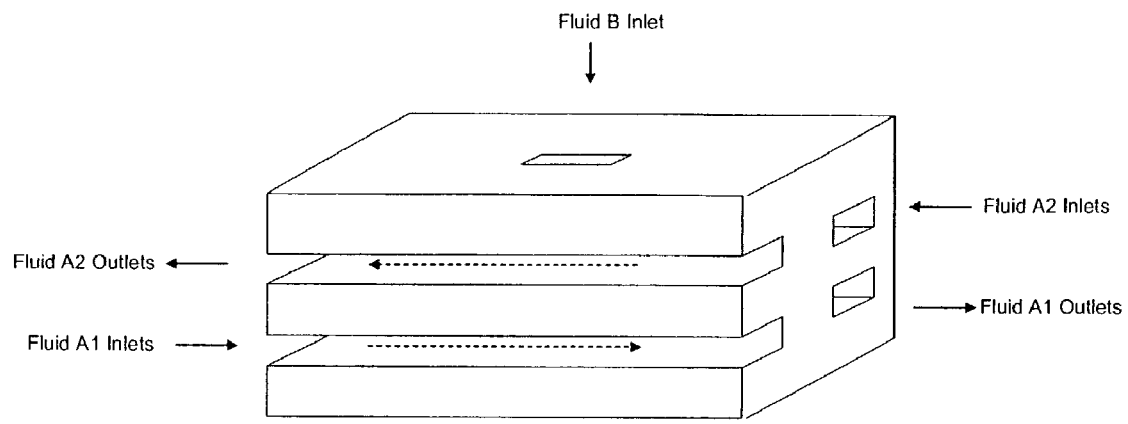

Another way to integrate heat exchange in an integrated reactor is illustrated schematically in FIGS. 4A and 4B. In this embodiment, a first reactant stream (Fluid A1, containing a hydrocarbon in the case of dehydrogenation) flows in a first direction (dashed arrow 47) through a first process channel 41 while a second reactant stream (Fluid A2, containing a hydrocarbon in the case of dehydrogenation) flows in an opposite direction (dashed arrow 46) in a second process channel. Heat exchange is provided to both process channels via an intervening, cross-flow heat exchange channel 43. Preferably, an appropriate catalyst 44, 45 (a dehydrogenation catalyst in the case of dehydrogenation) is disposed within each process channel 41, 42 on the process channel wall that is adjacent the heat exchange channel to form a reaction chamber within each process channel. The hot product stream exiting the reaction chamber is immediately quenched by thermal transfer with the incoming reactant stream in the adjacent process channel. The illustrated embodiments show the process channels as separated by a constant distance; however, it should be appreciated that the process channels could be positioned closer to each other in the recuperation zones (i.e., the zones where the process channels are adjacent, that is, the zones without an intervening heat exchange channel). Assigning length as the direction parallel to flow within each channel and height as the one direction that is perpendicular to flow in both the process channels and the heat exchange channel, and width being the remaining dimension, it is preferred that the length of each process channel be at least three times, more preferably 10 times longer than the width of the heat exchange channel; and, preferably, the preheat zone of the first process channel is of substantially the same length as the quench or "exhaust" zone of the second process channel, and vice versa. Preferably, the length of the preheat zone of each process chamber is preferably at least as long as the width of the heat exchange channel; similarly, the length of the quench zone of each process chamber is preferably at least as long as the width of the heat exchange channel. It can readily be appreciated that the capacity of this type of device can be increased by stacking up to any desired height with alternating heat exchange and process channels; in some embodiments at least 3 of each.

Figure 5A:
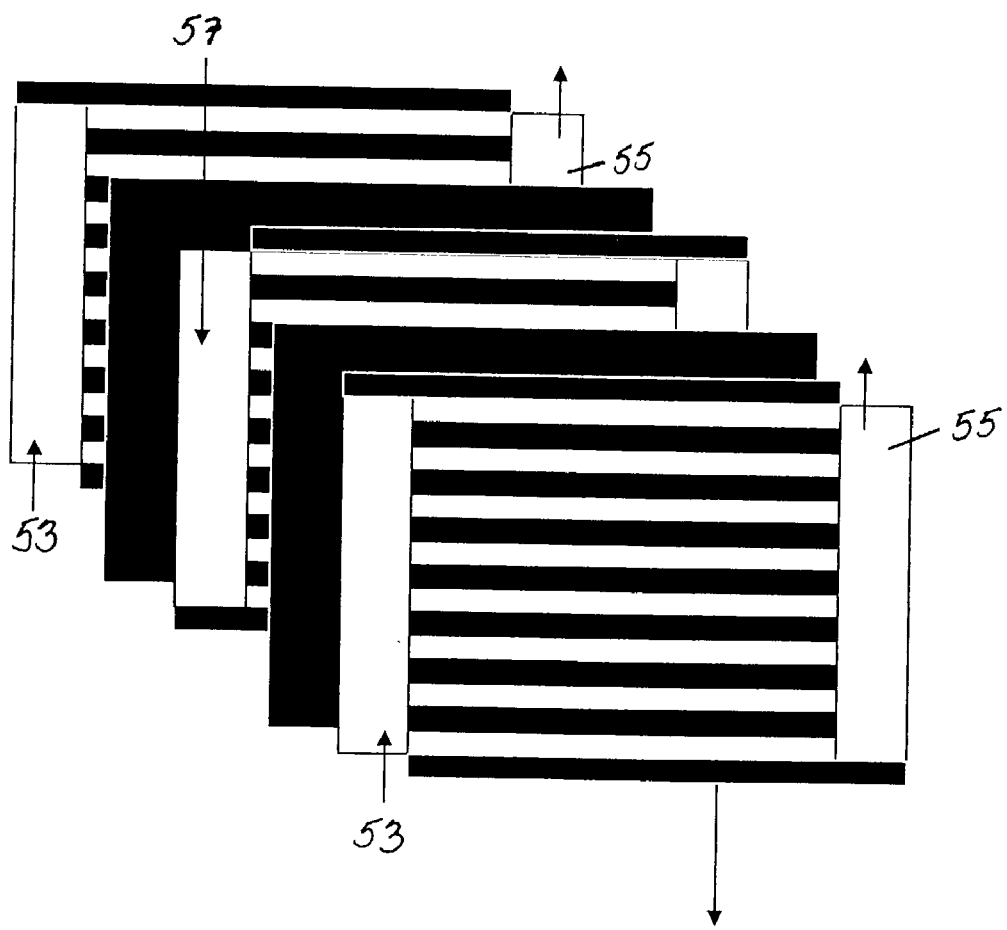
FIGS. 5A and 5B are schematic illustrations of integrated reactor designs that are "numbered up" to achieve greater capacity.

Sheets of channels and/or integrated reactors can be "numbered up" to obtain greater capacity. A schematic illustration of an exploded view of a stack of three identical sheets is shown in FIG. 5A. In a device formed by laminating these three sheets, a first fluid (such as a heated fluid) flows into inlet 53 through the first and third sheets and exits via outlet 55 while a process stream 57 (for example, containing a hydrocarbon) flows through the second sheet. In this figure, the dark regions indicate a solid material, while the white areas indicate areas for fluid flow (such as could be formed by etching). Flow occurs through all the channels. To further increase capacity, blocks 51 of multi-level reactors (see FIG. 5B) can be manifolded and operated together. It is advantageous to reduce temperature of the product stream as rapidly as possible after leaving the catalyst section of the microchannel reactor to prevent further undesirable reactions of the olefins. This rapid cooling is known as "quenching." An integrated or separate heat exchanger can be used to quench the reaction products, cooling them down rapidly once the reaction has taken place. For example, near the outlet of a reaction channel, cross-flow coolant channels can rapidly cool the product stream. In some preferred embodiments, the heat from the product stream is transferred to a hydrocarbon in a microchannel heat exchanger, thus preheating a hydrocarbon stream that can be subsequently dehydrogenated. The heat from the product stream could also be used to drive an endothermic reaction. Another form of quench is the rapid addition of a reactive (such as reactant feed) or a non-reactive gas into the hot product stream; this could be accomplished through a gas inlet or inlets located in a reaction chamber, or in or near a reaction chamber outlet, and, optionally with the aid of a static mixer structure within the downstream pipe.

In several of the methods and reaction systems described herein, the reaction products are quickly quenched below a temperature where carbon formation is no longer favored kinetically. Thus, the reaction zone may be closely and integrally linked with a heat exchange zone (either recuperative or other) to quickly cool the reaction mixture after the reactor to below 400° C. Integrated microchannel heat exchanger(s) preferably cool the reaction mixture at a rate greater than 1° C. per millisecond of average heat exchanger residence time; more preferably, at a rate greater than 5° C. per millisecond of average heat exchanger residence time. In some preferred embodiments, the temperature of the process stream decreases by 100, more preferably 200 and still more preferably 300° C. within 50 milliseconds (ms), more preferably 10 ms after reacting (that is, after passing through the hot reaction zone), and in some embodiments 1 ms to 500 ms, preferably 1 ms to 100 ms. Temperatures in reaction microchannels can be measured with thermocouples.

In some embodiments of the inventive reactor or method, the reactor (or method) is configured to send the product stream into a second reactor or recycle the product stream back into the same reactor.

In some preferred embodiments, walls of the reaction channels and/or inner surfaces of conduits and manifolds connected to the reaction channels are coated with a passivation layer. Passivation of surfaces inside the reaction chamber and/or in piping leading to, and/or especially piping leading from the reaction chamber reduces coking and can enhance time-on-stream performance. Passivation coatings have a different composition than the underlying material. Suitable passivation coatings include a refractory oxide such as silica, alumina, zirconia, titania, chromia, and ceria. In some preferred embodiments, the passivating coating has no inherent catalytic activity for dehydrogenation, olefin polymerization, cyclization and aromatization reactions leading to coking. The passivation coating could, optionally, be catalytic supports or could be dense coatings to protect an underlying metal wall. Passivation coatings can be made by applying a sol, or a fine particulate coating onto a metal surface, or applied by chemical or physical vapor deposition or electrochemical deposition, or thermally-grown, or combinations of these techniques.

The reaction channel contains a dehydrogenation catalyst. Suitable catalyst structures include porous catalyst materials, monoliths, washcoats, pellets, and powders. The catalyst can comprise a high surface area support and an overlying layer or layers comprising a catalytically active metal or metals. In some preferred embodiments, the reaction is heated by a combustion stream and, preferably, the heat exchange channel comprises a combustion catalyst that may contain structures such as porous catalyst materials, monoliths, washcoats, pellets, and powders.

The catalyst can fill up a cross-section of the reaction channel (a flow-through catalyst) or only occupy a portion of the cross-section of a reaction channel (flow-by). The use of a flow-by catalyst configuration can create an advantageous capacity/pressure drop relationship. In a flow-by catalyst configuration, gas preferably flows in a 0.1-1.0 mm gap adjacent to a porous insert or a thin layer of catalyst that contacts the microchannel wall (preferably the microchannel wall that contacts the catalyst is in direct thermal contact with a heat exchanger, preferably a heated fluid or exothermic reaction process stream contacts the opposite side of the wall that contacts the catalyst).

In one preferred embodiment, the reaction channel contains a porous catalyst material that defines at least a portion of at least one wall of a bulk flow path. In this preferred embodiment, the surface of the catalyst defines at least one wall of a bulk flow path through which the mixture passes. During operation, the mixture flows through the microchannel, past and in contact with the catalyst. The term "bulk flow path" refers to an open path (contiguous bulk flow region) within the reaction chamber. A contiguous bulk flow region allows rapid gas flow through the reaction chamber without large pressure drops. In preferred embodiments there is laminar flow in the bulk flow region. Bulk flow regions within each reaction channel preferably have a cross-sectional area of $5 \times 10\text{-}8$ to $1 \times 10^{-2}$ m$^2$, more preferably $5 \times 10^{-7}$ to $1 \times 10^{-4}$ m$^2$. The bulk flow regions preferably comprise at least 5%, more preferably 30-80% of either 1) the internal volume of the reaction chamber, or 2) the cross-section of the reaction channel. When a combustion reaction is used to heat the dehydrogenation reaction chamber in an integrated combustion reactor, the combustion reaction preferably contains a bulk flow path having the properties discussed above.

In some preferred embodiments, the catalyst is provided as a porous insert that can be inserted into (or removed from) each channel in a single piece; preferably the porous insert is sized to fit within a microchannel with a width of less than 2 mm. In some embodiments, the porous catalyst occupies at least 60%, in some embodiments at least 90%, of a cross-sectional area of a microchannel.

In another preferred embodiment, the catalyst is a coating (such as a washcoat) of material within a microchannel reaction channel or channels.

A "porous catalyst material" (or "porous catalyst") is a material having a pore volume of 5 to 98%, more preferably 30 to 95% of the total porous material's volume. At least 20% (more preferably at least 50%) of the material's pore volume is composed of pores in the size (diameter) range of 0.1 to 300 microns, more preferably 0.3 to 200 microns, and still more preferably 1 to 100 microns. Pore volume and pore size distribution are measured by Mercury porisimetry (assuming cylindrical geometry of the pores) and nitrogen adsorption. As is known, mercury porisimetry and nitrogen adsorption are complementary techniques with mercury porisimetry being more accurate for measuring large pore sizes (larger than 30 nm) and nitrogen adsorption more accurate for small pores (less than 50 nm). Pore sizes in the range of about 0.1 to 300 microns enable molecules to diffuse molecularly through the materials under most gas phase catalysis conditions. The porous material can itself be a catalyst, but more preferably the porous material comprises a metal, ceramic or composite support having a layer or layers of a catalyst material or materials deposited thereon. The porosity can be geometrically regular as in a honeycomb or parallel pore structure, or porosity may be geometrically tortuous or random. Preferred porous support materials include felts (nonwoven fibers or strands), foams (including a foam metal or foam ceramic), and honeycombs. The catalyst layers, if present, are preferably also porous. The average pore size (volume average) of the catalyst layer(s) is preferably smaller than the average pore size of the support. The average pore size in the catalyst layer(s) disposed upon the support preferably is in the range from 10-9 m to 10-7 m as measured by $N_2$ adsorption with BET method. More preferably, at least 50 volume % of the total pore volume is composed of pores in the size range of 10-9 m to 10-7 m in diameter. Diffusion within these small pores in the catalyst layer(s) is typically Knudsen in nature, whereby the molecules collide with the walls of the pores more frequently than with other gas phase molecules.

At a point where the chamber height or the chamber width is about 2 mm or less, the chamber height and the chamber width define a cross-sectional area. In some preferred embodiments, the cross-sectional area comprises a porous catalyst material and an open area, where the porous catalyst material occupies 5% to 95% of the cross-sectional area and where the open area occupies 5% to 95% of the cross-sectional area. In some preferred embodiments, the open area in the cross-sectional area occupies a contiguous area of $5\times10^{-8}$ to $1\times10^{-2} m^2$ The catalytically-active material in the process of the present invention is not particularly limited and may include any effective DH catalyst. Suitable catalytically-active materials of the present invention include Cr, Pt, Ni, Pd, a group VIII element, Ga, Mo, and W. The catalyst may contain additional components such as alkalai or alkaline earth promoters, Sn, Sb, In, Mo, and Bi. Preferred support materials include alumina (preferably stabilized alumina), silica, titania, other metal oxides, Zn or Mg spinels, tin oxide (for example tin oxide mixed with zirconia), mesoporous materials and zeolites. Of course, the catalyst may be comprised of combinations of these components.

The inventive methods result in the formation of $H_2$ and an unsaturated hydrocarbon or hydrocarbons. For example, ethane is converted to ethene, propane to propene, iso-butane to iso-butene, etc. Side products such as alkanes, polymers, coke, etc. are minimized; this minimization is reflected in the selectivities discussed below.

The level of hydrocarbon conversion is preferably at least 10%, preferably at least 20%, more preferably at least 30%, and in some embodiments 20 to 40%. The percent selectivity to desired product, in the process of the reaction, is preferably at least 50%, more preferably at least 65%, and still more preferably at least 80%. The yield of product alkene and/or arylalkene in mol % per cycle (where a cycle is defined as a single pass through a reaction chamber) is preferably greater than 10%, and more preferably greater than 20%. The specified levels of conversion, yield and selectivity should be understood as exemplary and include all values such as yield per cycle of at least 15%, at least 25%, etc. as well as yield ranges such as 10 to 35%, and selectivities such as at least 75%, and ranges such as 70 to 85%, etc. Further, it should be understood that preferred embodiments of the invention can be characterized by combinations of the characteristics described herein, for example, a hydrocarbon conversion of at least 20% and a selectivity of at least 65% at a LHSV of 32 $h^{-1}$.

Figure 6:
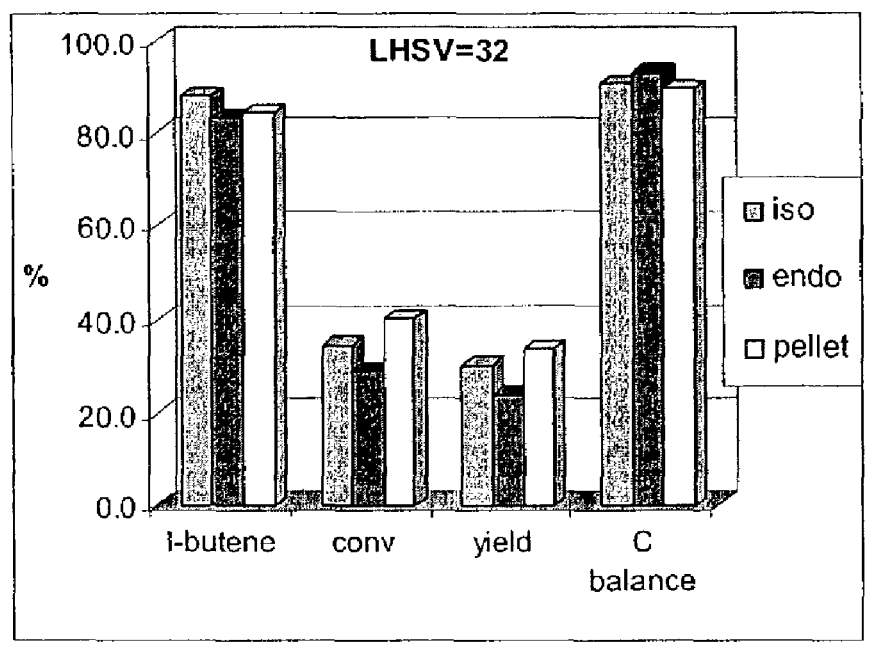
FIGS. 6 and 7 are histograms comparing iso-butene conversion and yield in a microchannel (labeled "pellet") versus larger channels (iso and endo) at LHSVs of 32 and 62. The "iso" data was an experimental variant but is not a good representative of conventional apparatus.
Figure 7:
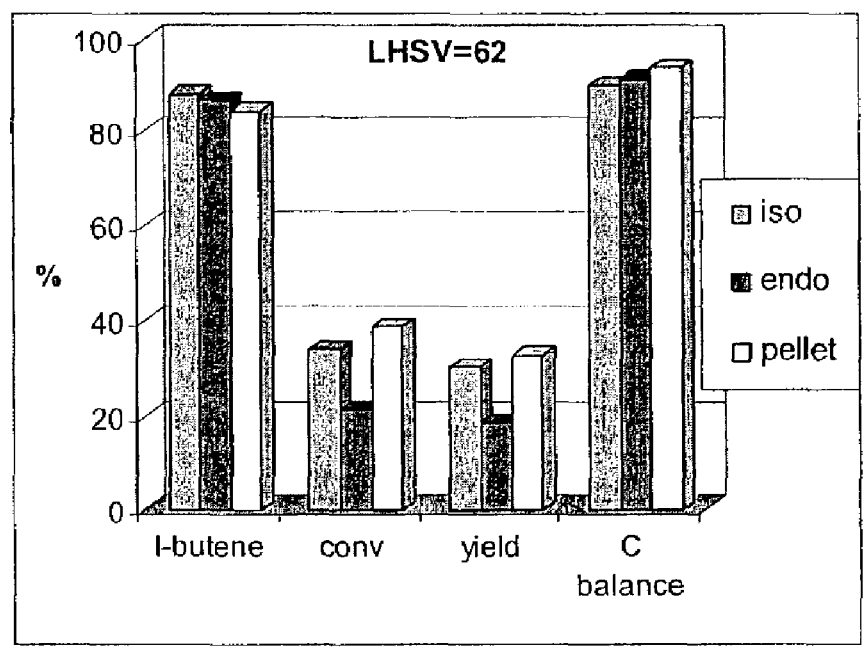
Figure 8:
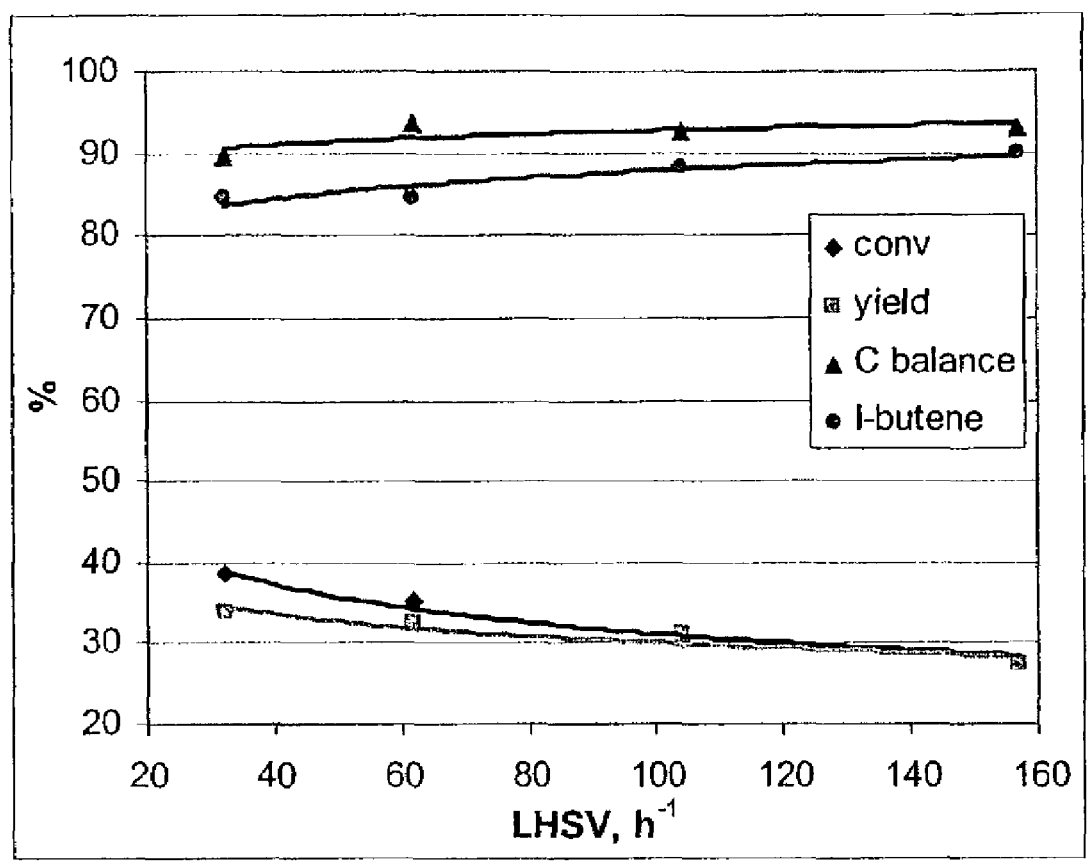
FIG. 8 shows conversion of isobutane and selectivity and yield of isobutene at varying LHSVs in a microchannel.
Figure 9A:
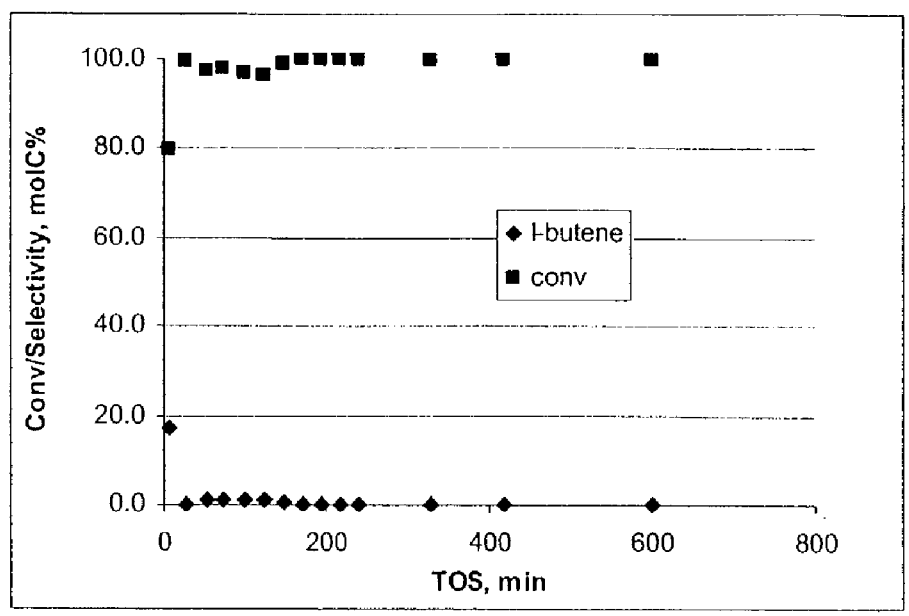
FIG. 9a shows the attempted dehydrogenation of isobutene in a non-passivated system.
Figure 9B:
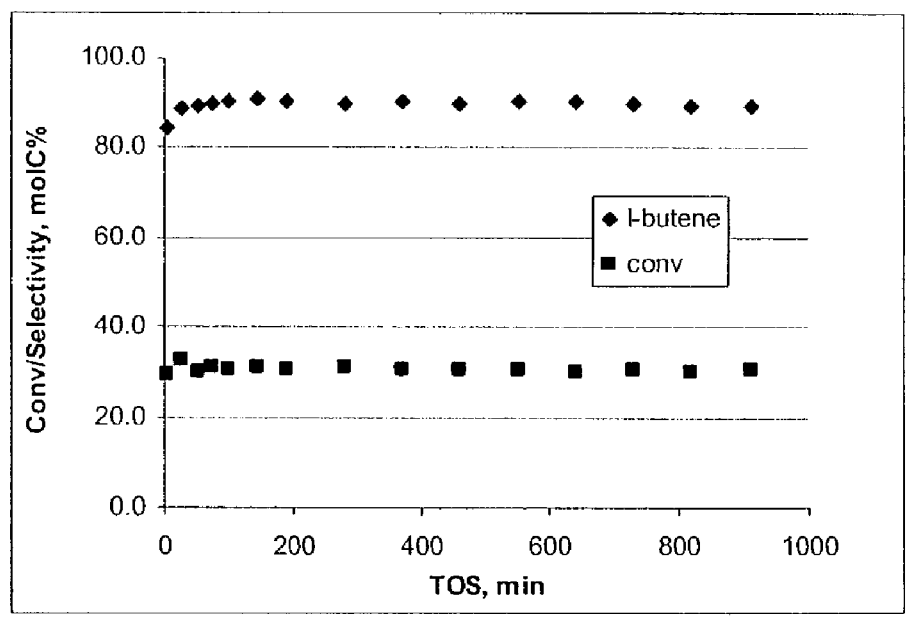
FIG. 9b shows conversion and selectivity data from dehydrogenation of isobutene for LHSV=157 in a passivated microchannel reactor.
Figure 10:
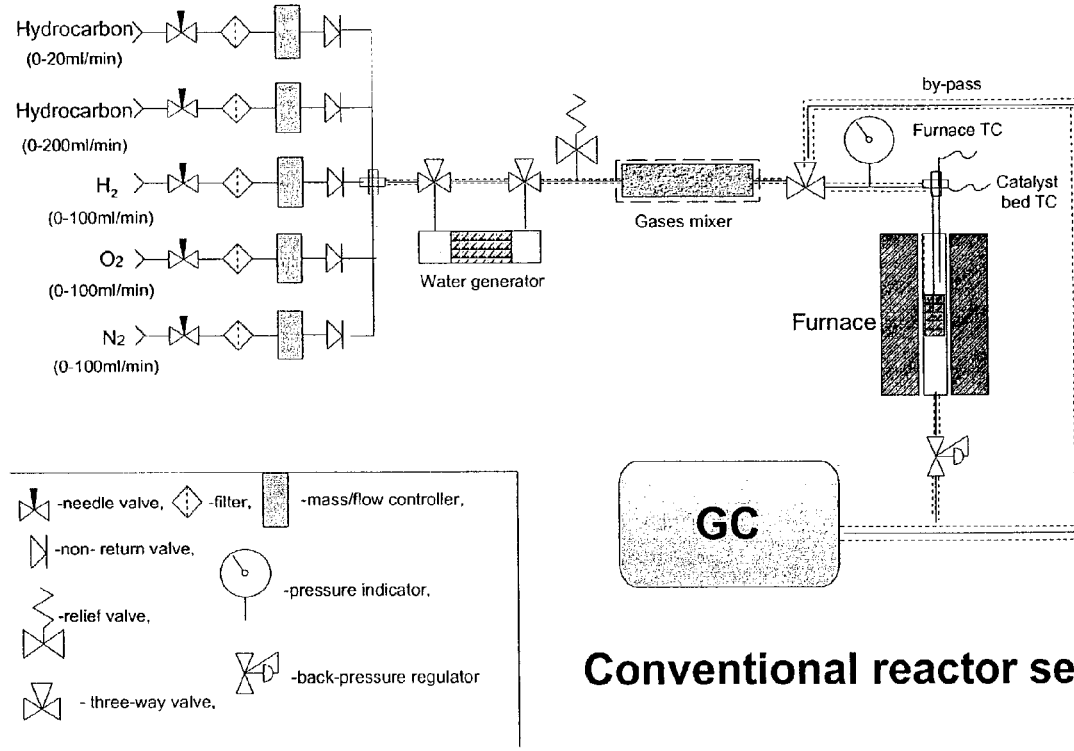
FIG. 10 schematically illustrates the reactor set-up used in the Examples.

Preferably the inventive methods and/or systems have stability such that when run continuously (without regeneration) for 10 hours at a LHSV of 32 (or, more preferably, 157) the yield of the desired alkene or arylalkene is at least 20% and diminishes by 20% or less (where LHSV is calculated based on the assumption that the reaction chamber volume is a constant). For example, if the yield is 30% at a point during a run, then after 10 hours continuous operation without regeneration the yield is at least 27%. More preferably, the inventive methods and/or systems have stability such that when run continuously (without regeneration) for 15 hours at a LHSV of 32 (or, more preferably, 157) the yield of the desired alkene or arylalkene is at least 25% and diminishes by 10% or less after 15 hours continuous operation without regeneration. These stability characteristics can be measured either from the start of a dehydrogenation run (using either freshly prepared catalyst or regenerated catalyst), or if the system exhibits some initial instability (such as shown in FIG. 6b), then the stability characteristic can be measured starting from a time after the system has stabilized.

The catalyst systems can be regenerated by treating the catalyst with an oxidant to oxidize reduced materials formed on or in the catalyst. Typical regeneration oxidants are oxygen or air. In some preferred embodiments, an integrated reactor will have multiple reaction channels and a regeneration process is conducted in one or more channels while a dehydrogenation process is conducted in one or more adjacent reaction channels; heat from the regeneration is used to drive the dehydrogenation. Alternatively, a hydrogenation system includes at least three reactors, one of which is in reaction mode, a second is regenerating, while a third reactor is in purge mode and cycling between the three reactors preferably, cycle times are at least 5 hours, more preferably at least 15 hours, and still more preferably at least 50 hours. For relatively long run times without regeneration, it can be more economical to run without continuous regeneration. In preferred embodiments, the catalyst and reactor remain stationary during regeneration, while valves are used to switch fluid flows to the regeneration and dehydrogenation reactions.

In some preferred embodiments, $H_2$ is removed during or after the dehydrogenation reaction. In a preferred method, the $H_2$ removed through a membrane. In some embodiments, the membrane forms a wall of the reaction channel.

The product alkene or aralkene can be separated from the process stream and either stored or used in a secondary reaction. A downstream membrane can be employed to separate hydrogen. In some preferred embodiments, separation is conducted within the same integrated device as the dehydrogenation.

The product stream, or more typically a portion of the product stream, can be redirected (recycled) back into the reaction channel or into another reaction channel to convert more of the reactant hydrocarbon(s) and thus increase yield. Typically, the desired alkene or arylalkene will be separated from the product stream and the unreacted hydrocarbon portion of the product stream recycled.

A product stream containing olefins and unconverted alkanes can be used without further separation as a feedstock for other processes including alkylation. In alkylation, (typically) olefins are reacted with isoalkanes to form higher branched alkanes with high octane numbers suitable for use as components of gasoline. Where the feedstock contains isobutane, the product stream is especially suited as an alkylation feedstock since the products include C3-C5 olefins and unconverted isobutane.

EXAMPLES

Catalyst

The preparation procedure and catalyst composition for Pt/Sn/Al$_2$O$_3$ catalyst was similar to that described in U.S. Pat. No. 4,430,517. The method is based on incipient wetness impregnation of gamma-alumina with aqueous solution of Pt and Sn. Generally, $H_2PtCl_6 \cdot xH_2O$ and $SnCl_4$ are dissolved in aqueous solution of HCl forming $(PtCl_2(SnCl_3)_2)_2$— complex. The solution is impregnated and then the water is evaporated from the sample by heating it to 90° C. for 1.5 h and then to 120° C. for 30 min. The catalyst was calcined at 500° C. in a flow of air (80 ml/min) for 2 h. The BET surface area and pore volume of the neutral activated gamma alumina (Aldrich) was found to be 163 $m^2$/g and 0.26 ml respectively. The concentration of the HCl in the water was made 2.5 wt %. A batch of catalyst typical of that used in these experiments, the amounts were as follows: Pt acid: 0.504 g; $SnCl_4$: 0.165 g; HCl: 0.096 g; $H_2O$: 3.61 g; $Al_2O_3$: 14.8 g. ICP analysis: Pt 0.75 wt %; Sn 0.4 wt %; Pt:Sn=1.4:1 atomic ratio (patent 1:1);

BET analysis of catalyst after calcining: 147 m²/g. The particle size of the catalyst was between 650-800 μm in the comparative examples and between 250-400 μm for use in the "microchannel" examples. The catalyst was packed into a reaction chamber (either microchannel or comparative examples) and activated by heating to 500° C. in flowing $O_2$ (40 ml/min) for 1 h followed by heating at 450° C. in flowing $H_2$ (60 ml/min) for 2 h.

Reaction Conditions

The reaction was conducted at 550° C. and the reactant stream was a 1:3 molar ratio of iso-butane:$H_2$ for LHSVs up to 32, and 1:2 molar ratio of iso-butane:$H_2$ for LHSVs above 32. A schematic view of the testing apparatus is shown in FIG. 1. LHSV was calculated based on the volume occupied by the catalyst.

COMPARATIVE EXAMPLES

The comparative examples were carried out in a fixed-bed, quartz tube reactor with an internal diameter of 10 mm. Temperature of the reaction was controlled with either the catalyst at constant temperature, as measured by a thermocouple, within the catalyst bed (labeled "isothermal" in Table 1), or in function of LHSV in a microchannel and in more conventionally sized apparatus. It was surprisingly discovered that conducting the dehydrogenation reaction in a microchannel resulted in a significantly higher conversion and a significantly higher yield of the desired iso-butene for both 32 and 62 LHSV. Furthermore, it is not conventional, or indeed possible, to run under "isothermal" conditions in conventional fixed bed reactors, rather, the "endothermic" conditions are a better model of a conventional system. Thus, we have surprisingly found that the microchannel reactor can be operated at LHSV above 100 and still achieve substantially higher conversion and yield of olefins than a conventional fixed bed reactor operating at much lower LHSV.

In both the microchannel and the fixed-bed, quartz tube reactors it was found that isobutene selectivity decreased with increasing contact time.

In initial tests with the microchannel apparatus, and no catalyst, it was found that a significant amount of coke formed at the union of the reactor block with a tube. The union was made of Inconel 600 which is an active catalyst for carbonization of hydrocarbons and olefins. This problem was eliminated by coating with a silica passivation layer that was applied by chemical vapor deposition.

TABLE 1

|  | Comparative reactor | | | | Microchannel reactor | | | |
| --- | --- | --- | --- | --- | --- | --- | --- | --- |
|  | isothermally | | endothermally | | | | | |
| LHSV | 32 | 62 | 32 | 62 | 32 | 62 | 104 | 157 |
| Methane | 4.5 | 3.6 | 4.9 | 4.3 | 5.2 | 5.6 | 5.6 | 3.3 |
| Ethane | 0.0 | 0 | 0 | 0 | 0.6 | 0.5 | 0.5 | 0 |
| Propene | 0.5 | 0.7 | 0.8 | 1.8 | 0.7 | 1.0 | 0.8 | 0.9 |
| Propane | 2.4 | 2.7 | 4.6 | 3.1 | 2.5 | 3.8 | 1.9 | 3.9 |
| n-butane | 3.6 | 3.4 | 5.1 | 3.1 | 4.7 | 3.1 | 1.6 | 1.2 |
| 1-butene | 0.2 | 0.5 | 0.3 | 0.2 | 0.6 | 0.5 | 0.4 | 0.3 |
| trans-2-butene | 0.8 | 0.7 | 0.9 | 0.7 | 0.8 | 0.7 | 0.5 | 0.4 |
| cis-2-butene | 0.0 | 0 | 0 | 0.2 | 0.5 | 0.4 | 0.3 | 0.0 |
| 1-butene | 87.9 | 88.2 | 83.3 | 86.7 | 84.3 | 84.5 | 88.3 | 90.0 |
| conv | 34.6 | 34 | 29 | 21 | 40.0 | 38.4 | 35.3 | 30.4 |
| yield | 30.4 | 30 | 24 | 18 | 33.8 | 32.5 | 31.2 | 27.3 |
| C balance | 90.8 | 90 | 93 | 91 | 89.6 | 93.7 | 92.6 | 93.0 | adiabatic mode wherein the control thermocouple was within the gas phase immediately prior to entering the bed (labeled "endothermic" in Table 2). Catalyst volume varied from 0.2 to 0.7 ml.

"MICROCHANNEL" EXAMPLES

In these examples (labeled "pellet in FIGS. 2-3), the catalyst was packed in a rectangular slot having dimensions: channel gap: 0.02"; and channel length of 2". The channel had a width of 0.375". The channel was drilled in a metal (Inconel 625) cylinder having dimensions of 0.5 inch diameter x 2 inch long. The catalyst amounts were as follows:

| LHSV = 32; | cat. weight = 0.056 g; | cat. vol (calculated) = 0.077 ml |
| --- | --- | --- |
| 62 | 0.05 g | 0.068 ml |
| 104 | 0.05 g | 0.068 ml |
| 157 | 0.024 g | 0.033 ml |

The results of testing are shown below in Table 1 and in graphic form in FIGS. 2-5. FIG. 4 shows performance as a In initial testing, with no catalyst, an untreated Inconel 625 slotted cylinder was tested with flowing hydrogen and isobutene (2:1) at 550° C. The channel coked in about 7 hours and yielded very poor results. Subsequently, a fresh Inconel 625 slotted cylinder was wash-coated with an alumina sol, dried with a 10 minute ramp up to 200° C., and calcined at 900° C. for 12 hours. The resulting, passivated reactor did not coke in 7 days of operation at the same conditions (flowing hydrogen and isobutene (2:1) at 550° C.).

Another problem encountered during testing was that uncoated piping leading from the reaction chamber coked within 20 minutes and yield fell to zero. Passivating the piping with vapor deposited silica alleviated this problem.

Figure 5B:
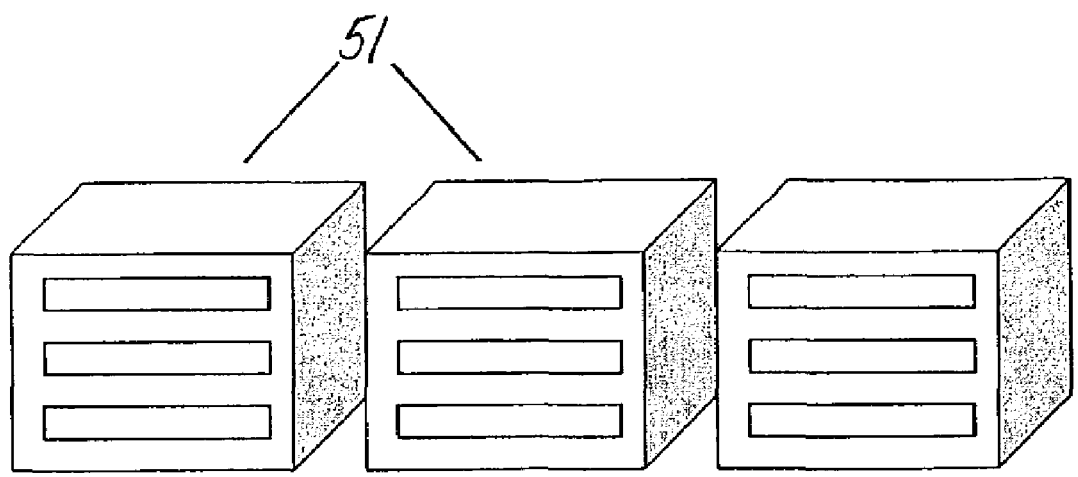

Conversion and selectivity data from dehydrogenation of isobutene for LHSV=157 (through a catalyst) in a passivated microchannel reactor is illustrated in FIG. 5b. Performance was slightly unstable in the first 50 minutes but remained essentially unchanged in the period from 50 minutes to at least 900 minutes.

We claim:

1. A method of dehydrogenating a hydrocarbon, comprising:

passing a reactant stream comprising a gaseous hydrocarbon into a reaction chamber comprising a dehydrogenation catalyst and wherein the reaction chamber has an internal dimension of 2 mm or less;

wherein the reactant stream is passed into the reaction chamber at a LHSV of at least 32;

dehydrogenating the hydrocarbon within the reaction chamber to form a product stream comprising an olefin;

wherein after 15 hours of continuous operation, at least 75% of the equilibrium conversion of the hydrocarbon to an olefin is achieved and wherein the yield of olefin diminishes by 10% or less over the course of the 15 hours of continuous operation and wherein the yield of olefin remains at least 25% or more.

2. The method of claim 1 wherein selectivity to an unsaturated hydrocarbon is at least 65%.

3. A method of dehydrogenating a hydrocarbon, comprising:

passing a reactant stream comprising a gaseous hydrocarbon into a reaction chamber comprising a dehydrogenation catalyst and wherein the reaction chamber has an internal dimension of 2 mm or less;

dehydrogenating the hydrocarbon within the reaction chamber to form a product stream comprising an olefin; wherein the yield of olefin decreases by less than 50% at from 0.2 and 20 hours of continuous operation without regeneration.

4. The method of claim 3 wherein the yield of olefin decreases by less than 20% at from 0.2 and 20 hours of continuous operation without regeneration.

5. The method of claim 3 wherein the reactant stream consists essentially of $C_2$-$C_{18}$ alkanes.

6. The method of claim 1 wherein there is no $H_2$ in the reactant stream.

7. The method of claim 3 wherein the reactant stream has essentially no steam.

8. The method of claim 7 wherein the reactant stream comprises at least 75% of propane, and the step of dehydrogenating is conducted in the temperature range of 450 to 700° C.

9. The method of claim 1 wherein the reactant stream comprises at least 75% of isobutane and the step of dehydrogenating is conducted in the temperature range of 400 to 650° C.

10. The method of claim 1 wherein the LHSV is at least 64 $h^{-1}$.

11. The method of claim 7 wherein the reactant stream comprises essentially no diluents.

12. The method of claim 1 wherein downstream pipework is connected to the reaction chamber and wherein fluid flow rate in the downstream pipework is the same or higher than in the reaction chamber and is 50 ms or less.

13. The method of claim 3 further comprising a step of selectively removing $H_2$ during reaction by a $H_2$-permeable membrane.

14. The method of claim 3 wherein a wall separates the reaction chamber from a combustion channel, wherein the combustion channel comprises a combustion catalyst on the wall that separates the reaction chamber from the combustion channel; and further comprising a fuel or oxidant channel;

wherein apertures connect the combustion and fuel or oxidant channels; and wherein fuel or an oxidant in the fuel or oxidant channel flows into the combustion channel through the apertures and combusts on the combustion catalyst to provide heat for the step of dehydrogenating.

15. The method of claim 3 wherein a diluent is added in a distributed fashion along a length of the reaction chamber.

16. The method of claim 15 wherein the diluent is hot in order to boost hydrocarbon conversion.

17. The method of claim 15 wherein the diluent is cold to rapidly quench the reaction.

18. The method of claim 1 wherein the yield per cycle is greater than 20%.

19. The method of claim 3 wherein the hydrocarbon conversion is at least 20% and the selectivity to desired product is at least 65%.

20. The method of claim 1 wherein the step of dehydrogenating occurs in an integrated reactor wherein a catalyst regeneration process is conducted in an adjacent channel and heat from the regeneration process is used to drive the step of dehydrogenating.

21. The method of claim 3 wherein the reactant stream comprises isobutene and further wherein the product stream is used without separation as a feedstock for an alkylation process.

22. The method of claim 1 wherein the LHSV is greater than 100 $h^{-1}$ and wherein the reaction chamber comprises surfaces passivated with a refractory oxide.

23. The method of claim 12 wherein the downstream pipework comprises surfaces passivated with a refractory oxide.

* * * * *